(12) United States Patent
Badeau et al.

(10) Patent No.: US 10,578,589 B2
(45) Date of Patent: Mar. 3, 2020

(54) SYSTEM AND METHOD FOR ULTRASOUND INSPECTION WITH TIME REVERSAL

(71) Applicants: Nicolas Badeau, Quebec (CA); Guillaume Painchaud-April, Quebec (CA); Benoit Lepage, L'Ancienne-Lorette (CA)

(72) Inventors: Nicolas Badeau, Quebec (CA); Guillaume Painchaud-April, Quebec (CA); Benoit Lepage, L'Ancienne-Lorette (CA)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 107 days.

(21) Appl. No.: 15/994,528

(22) Filed: May 31, 2018

(65) Prior Publication Data

US 2018/0348170 A1  Dec. 6, 2018

Related U.S. Application Data

(60) Provisional application No. 62/513,558, filed on Jun. 1, 2017.

(51) Int. Cl.
*G01N 29/04* (2006.01)
*G01N 29/44* (2006.01)
(Continued)

(52) U.S. Cl.
CPC ......... *G01N 29/262* (2013.01); *G01N 29/043* (2013.01); *G01N 29/069* (2013.01);
(Continued)

(58) Field of Classification Search
CPC .. G01N 29/262; G01N 29/043; G01N 29/069; G01N 29/07; G01N 29/4463;
(Continued)

(56) References Cited

U.S. PATENT DOCUMENTS

| 2007/0008026 A1* | 1/2007 | Lin ................... H03K 3/35613 |
| | | 327/309 |
| 2013/0068026 A1* | 3/2013 | Kitazawa ............. G01N 29/043 |
| | | 73/602 |

(Continued)

FOREIGN PATENT DOCUMENTS

EP          02985600      *   2/2016

OTHER PUBLICATIONS

B. Beardsley et al, A Simple Scheme for Self-Focusing of an Array, Journal of Nondestructive Evaluation, vol. 14, No. 4, 1995, p. 169-179.

(Continued)

*Primary Examiner* — Jacques M Saint Surin
(74) *Attorney, Agent, or Firm* — Gerald P. Kazanjian (57) ABSTRACT

Disclosed is a system and method of determining the test surface profile and compensating the gain amplitude when using time reversal focal laws in ultrasound non-destructive testing. Computer simulations are used to compute the diffraction field at time of incidence of the transmitted parallel wave front on the test surface. Knowledge of the surface profile and the diffraction field allows determination of coverage at the test surface and improved accuracy of flaw sizing.

22 Claims, 9 Drawing Sheets

(51) Int. Cl.
    *G01N 29/07* (2006.01)
    *G01N 29/06* (2006.01)
    *G01N 29/26* (2006.01)
(52) U.S. Cl.
    CPC ......... *G01N 29/07* (2013.01); *G01N 29/4436* (2013.01); *G01N 29/4463* (2013.01); *G01N 2291/011* (2013.01); *G01N 2291/044* (2013.01); *G01N 2291/106* (2013.01)
(58) Field of Classification Search
    CPC ......... G01N 29/4436; G01N 2291/106; G01N 2291/044; G01N 2291/011
    USPC .......................................................... 73/625
    See application file for complete search history.

(56) References Cited

U.S. PATENT DOCUMENTS

| | | | | |
|---|---|---|---|---|
| 2014/0157903 A1* | 6/2014 | Oberdoerfer | ........ | G01N 29/069 73/632 |
| 2014/0202250 A1* | 7/2014 | Murakoshi | ............ | G01N 29/04 73/632 |
| 2014/0283611 A1* | 9/2014 | Habermehl | .......... | G01N 29/069 73/602 |

OTHER PUBLICATIONS

Mathias Fink, Time Reversal of Ultrasonic Fields—Part I: Basic Principles, IEEE Trans. on Ultrasonics, Ferroelectrics & Frequency Control, vol. 39, No. 5, 1992, p. 555-566.

\* cited by examiner

SYSTEM AND METHOD FOR ULTRASOUND INSPECTION WITH TIME REVERSAL

CROSS-REFERENCE TO RELATED APPLICATIONS

This application claims the benefit and priority of U.S. Provisional patent application Ser. No. 62/513,558 filed Jun. 1, 2017 entitled IMPROVED SYSTEM AND METHOD FOR ULTRASOUND INSPECTION WITH TIME REVERSAL, the entire disclosure of which is incorporated herein by reference.

FIELD OF THE INVENTION

The invention relates in general to non-destructive testing and inspection (NDT/NDI) with phased array (PA) ultrasound, and in particular to a system and method of determining the test surface profile and compensating the gain amplitude when using time reversal focal laws.

BACKGROUND OF THE INVENTION

Use of time reversal focal laws is a known method of inspecting complex surfaces with a PA probe. See, for example, Beardsley, B. et al. 1995. 'A Simple Scheme for Self-Focusing of an Array', Journal of Nondestructive Evaluation, Vol. 14, No. 4 (1995), p 169-179 and 'Time Reversal of Ultrasonic Fields—Part I: Basic Principles', Mathias Fink, IEEE Transaction on Ultrasonics, Ferroelectrics, and Frequency Control, Vol. 39, No. 5, September 1992, p 555-566. The method involves creating an incident acoustic wave front which is parallel to the surface being inspected, the parallel wave front allowing improved resolution for imaging sub-surface flaws. The parallel wave front is iteratively created as the PA probe is scanned along the test surface, the iteration involving forming focal laws with a time-reversal algorithm which reverses the arrival time at the probe of acoustic echoes reflected from the test surface.

When the time-reversal algorithm is used, the focal laws are adapted at each probe scan position in order to create a wave front having normal incidence at every point on the surface. However, since the focal laws are changing continuously during the scan, any calibration procedure performed with a particular focal law is invalidated. In particular, the calibration gain, which defines the inspection sensitivity, is heavily dependent on the focal laws, and will therefore change in the course of the scan. The part coverage and the flaw sizing accuracy also depend on the focal laws, and will therefore also change in the course of the scan. There is no known method in existing practice to compensate for the changes in calibration gain, part coverage and flaw sizing accuracy.

Another problem with the time reversal algorithm is that the delays computed cannot be directly used to obtain the profile of the test surface because the wave front created by the focal laws is a combination of several wave fronts, namely the wave fronts of each of the transmitting elements. It is necessary to have detailed knowledge of the surface profile because it allows the user to ensure complete coverage of the test surface and to more precisely determine flaw size and position within the test object.

SUMMARY OF THE INVENTION

Accordingly, it is a general objective of the present disclosure to ensure reliable calibration of inspections which use the reverse algorithm procedure.

It is further an objective of the present disclosure to make an accurate determination of the test surface profile.

It is further an objective of the present disclosure to maintain calibration reliability by compensating for amplitude changes due to changes of focal laws during the course of the inspection.

It is further an objective of the present disclosure to improve flaw sizing accuracy. by compensating for amplitude changes due to changes of focal laws during the course of the inspection.

It is further an objective of the present disclosure to determine the test surface coverage for all positions of the scan during the course of the inspection, so that it will be apparent to the user whether or not the entire surface has been adequately inspected.

Note that it is necessary to have an accurate determination of the test surface profile in order to achieve the objectives of compensating amplitude changes, improving flaw sizing accuracy and determining test surface coverage.

The foregoing objectives are achieved with a system and method for:

- Conducting a time reversal on front wall inspection routine in order to compute time reversal delays corresponding to a wave front which is normal to the test surface, and applying the time reversal delays to initial A-scans to produce delayed A-scans.
- Using the time reversal delays and a set of inspection parameters in conjunction with computer simulation tools to compute the diffraction field of the wave front at the time of incidence on the part surface.
- Obtaining the profile of the test surface from the wave front diffraction field.
- Using the test surface profile, the time reversal delays and the inspection parameters to compute the sensitivity of each receiver aperture to the reflected wave front, the computation being done using computer simulation tools.
- Computing the compensation gain from the sensitivity, and applying the compensation gain to the delayed A-scans. This step compensates for the gain variation caused by the change of focal laws along the scan axis.
- Computing the part coverage using the amplitude of the incident wave front along the test surface.
- Using the test surface profile and the probe surface profile (known from the inspection parameters) to compute more precisely the sizes of flaws and indications.

DETAILED DESCRIPTION OF PREFERRED EMBODIMENT

Figure 1A:
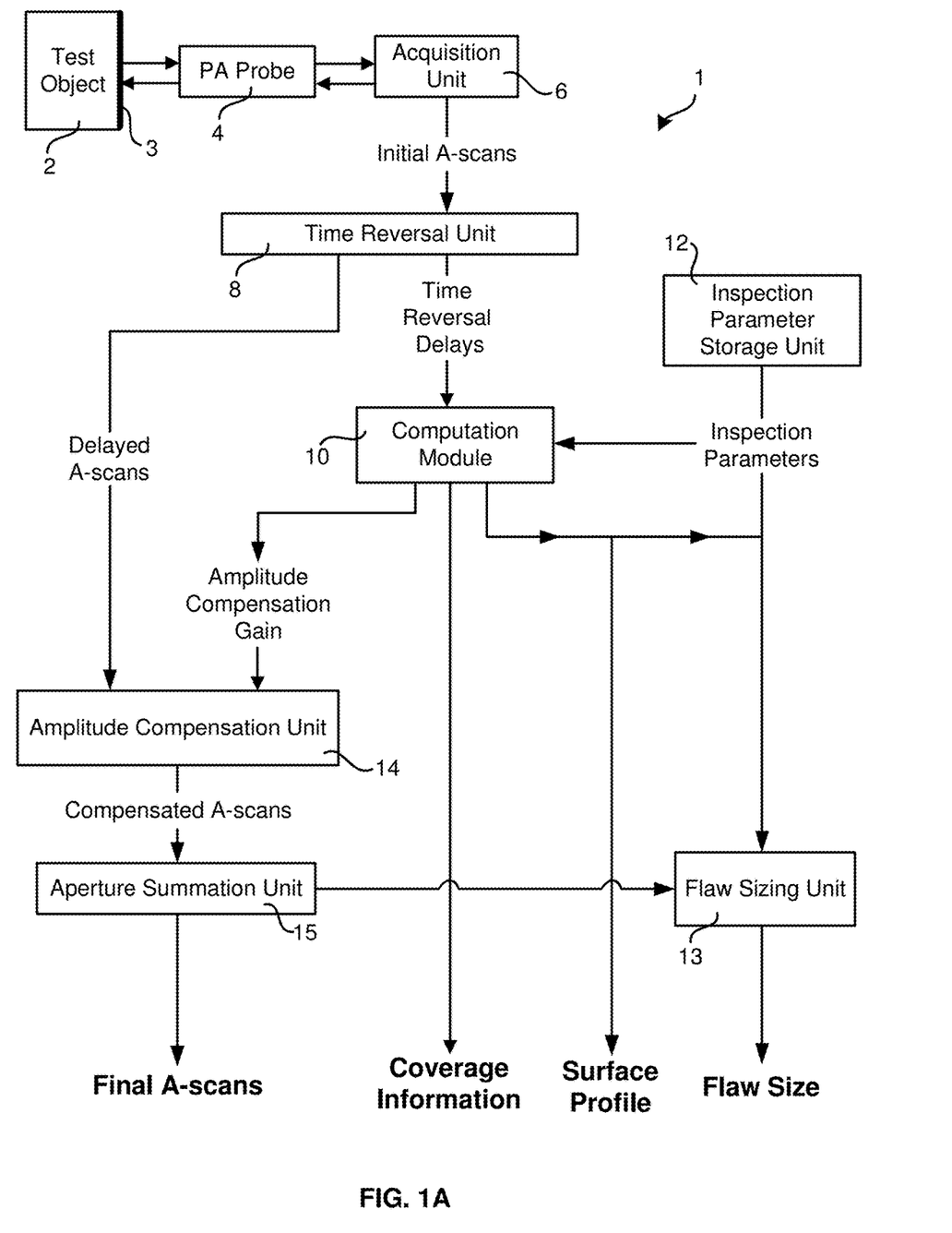
FIG. 1A is a schematic of a first embodiment of an improved time reversal system according to the present disclosure.

FIG. 1A is a schematic of an improved time reversal system 1 according to the present disclosure. A PA probe 4 comprises a multiplicity of probe elements which transmit acoustic energy into a test surface 3 of a test object 2 and receive echo signals reflected from test surface 3 or from flaws within test object 2. Elements of PA probe 4 which are transmitting acoustic energy may be configured in one or more transmitter apertures. In an embodiment, the transmitter aperture may comprise all the elements of probe 4, however other configurations of transmission are possible and are within the scope of the present disclosure. An acquisition unit 6 controls transmission from probe 4 and receives the echo signals. Acquisition unit 6 outputs initial A-scans, which are plots of echo signal amplitude vs receive time. In an embodiment, all the probe elements are receiving elements, in which case there is one initial A-scan for each probe element. However, other configurations of receiving elements are possible and are within the scope of the present disclosure. The initial A-scans are received by a time reversal unit 8 which calculates time reversal delays based on the arrival time of echo signals from test surface 3 at each of the receiving elements. The corresponding time reversal delay is applied to each transmitting element such that the transmitted wave front is parallel to test surface 3. Applying the corresponding time reversal delays to the initial A-scans produces a set of delayed A-scans.

A computation module 10 receives the time reversal delays from time reversal unit 8 and a set of inspection parameters from an inspection parameter storage unit 12. Computation module 10 outputs an amplitude compensation gain which is applied by an amplitude compensation unit 14 to the delayed A-scans, thereby producing a set of compensated A-scans which are amplitude compensated such that the amplitudes of the compensated A-scans are representative of the size of a flaw located at any position below test surface 3 within test object 2. This amplitude correction is performed in order to make the front wall amplitude profile uniform to a specific amplitude level, either a calibrated level or a user chosen level.

The compensated A-scans are received by an optional aperture summation unit 15, which employs a set of user defined receiver apertures, each receiver aperture comprising a plurality of receiver elements. Aperture summation unit 15 sums the compensated A-scans corresponding to the receiver elements of each receiver aperture, the summation taking into account the time reversal delay offsets between the elements of each receiver aperture. The output of aperture summation unit 15 is a set of final A-scans, there being one final A-scan for each receiver aperture. The purpose of summing the compensated A-scans to produce the final A-scans is to reduce noise by averaging in the summation.

The following description of a simple summation is by way of example only. If probe 4 has 8 receiver elements, the receiver elements being designated elements 1 through 8, then a simple summation into 6 receiver apertures each comprising 3 elements may be made by summing the compensated A-scans of elements 1, 2 and 3, elements 2, 3 and 4, elements 3, 4 and 5, elements 4, 5 and 6, elements 5, 6 and 7, and elements 6, 7 and 8. Note that the foregoing summation example is not intended to be limiting in any way. Probe 4 may have any number of elements, there may be any number of receiver apertures and there may be any number of elements in each receiver aperture.

Computation module 10 also outputs a surface profile, which is an accurate mapping of the profile of test surface 3, and coverage information, which is a mapping of locations on test surface 3 where the corrected amplitude of the diffraction field falls below a user defined threshold.

Note that the final A-scans, the amplitude compensation gain, the surface profile and the coverage information are all updated in real time as probe 4 is mechanically scanned along test surface 3 of test object 2.

A flaw sizing unit 13 receives the final A-scans from aperture summation unit 15, the test surface profile from computation module 10 and the inspection parameters from inspection parameter storage unit 12. Using information from an aperture sensitivity computation unit 18 (see FIG. 1C), flaw sizing unit transposes a detected flaw from its observed size at the surface of probe 4 to its actual size at or below test surface 3. The output of flaw sizing unit 13 is an improved determination of a flaw size.

Figure 1B:
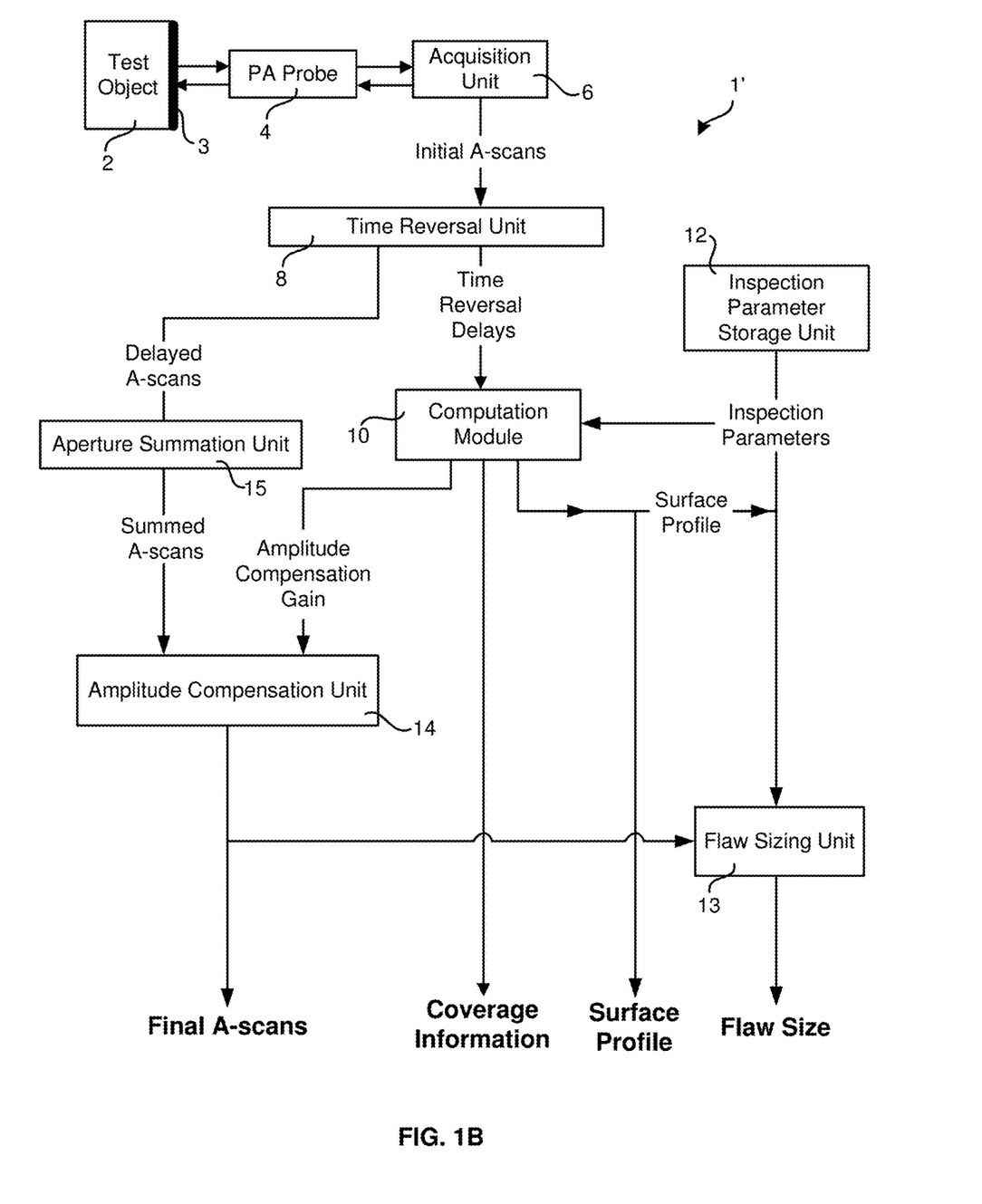
FIG. 1B is a schematic of a second embodiment of an improved time reversal system according to the present disclosure.

FIG. 1B is an alternative embodiment of an improved time reversal system 1' according to the present disclosure. Elements of time reversal system 1' are the same as those of the system 1 of FIG. 1A, with the exception of optional aperture summation unit 15 which is located prior to amplitude compensation unit 14 in system 1'. Therefore, in system 1', summation into receiver apertures is done with uncompensated delayed A-scans, and compensation of the summed A-scans is subsequently performed by amplitude compensation unit 14 to produce the final A-scans.

Figure 1C:
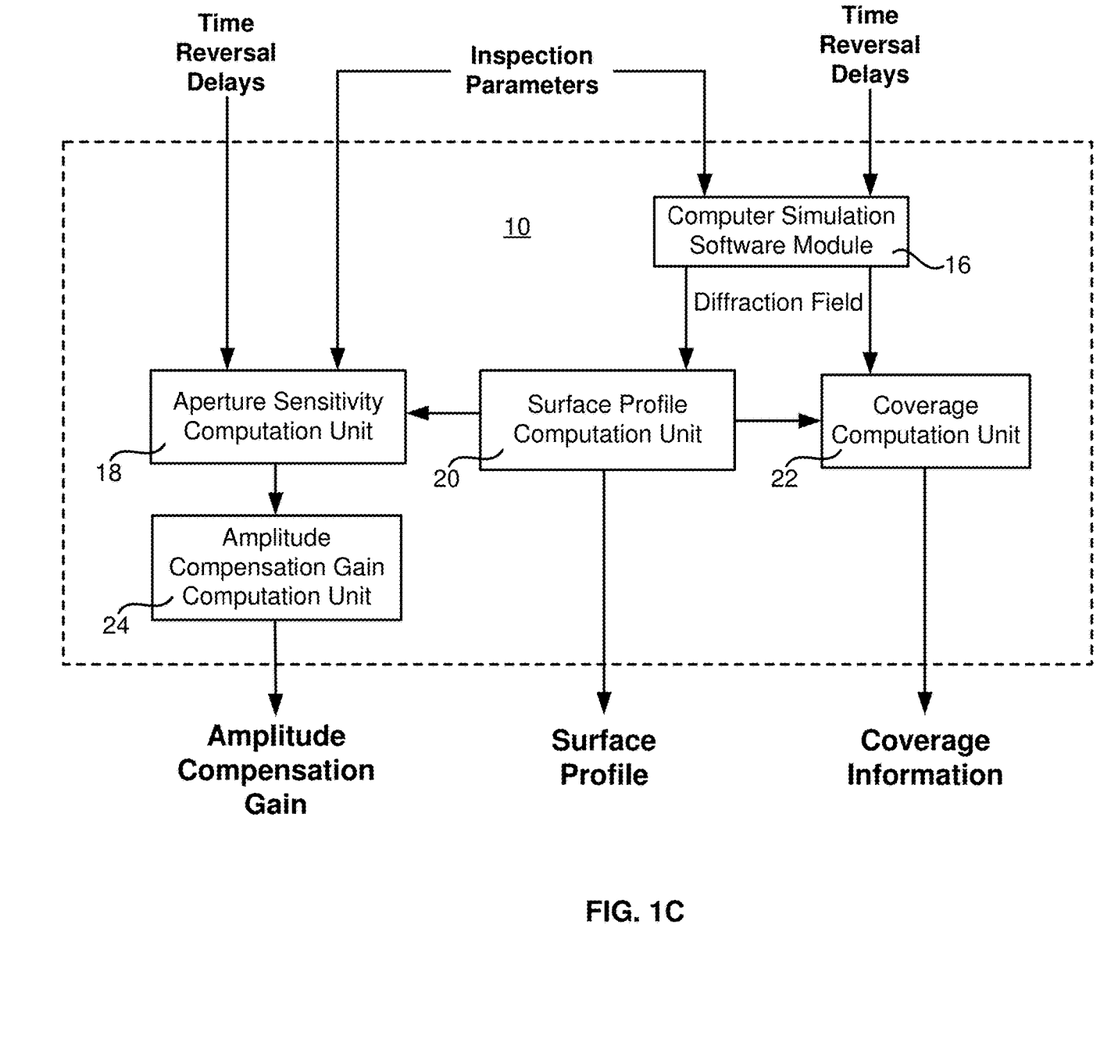
FIG. 1C is a schematic of a computation module according to the present disclosure.
Figure 4:
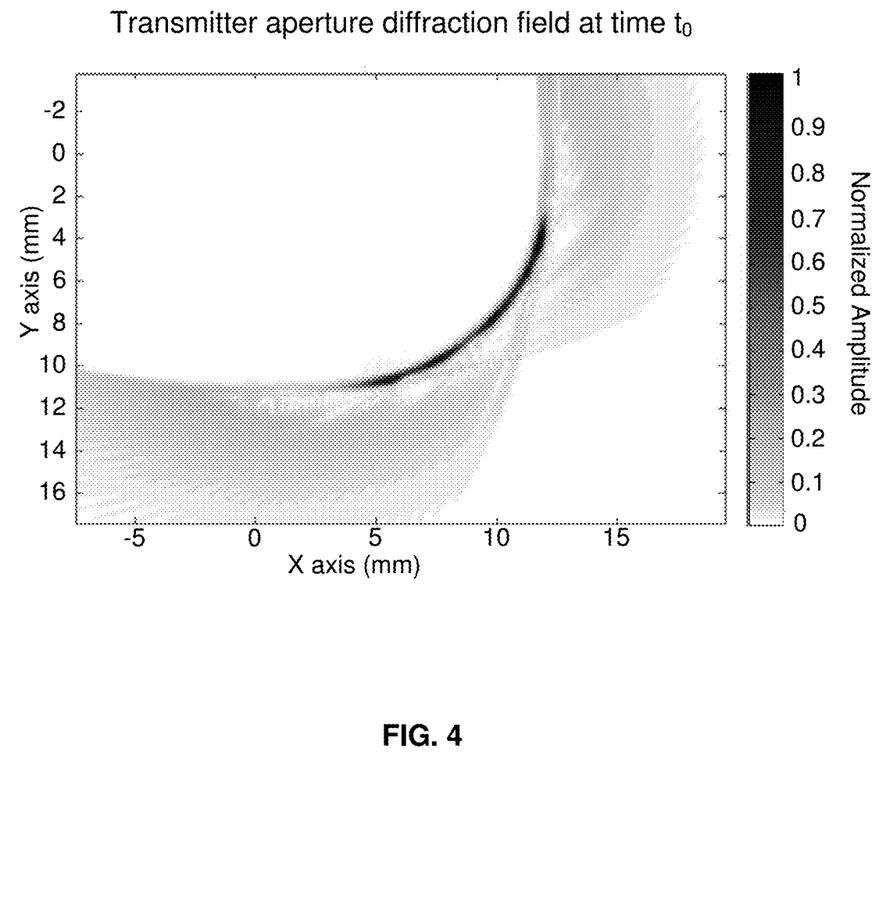
FIG. 4 is an illustration of the diffraction field of a wave front at time of incidence on a test surface for the curved probe illustrated in FIG. 3A.

FIG. 1C is a schematic of computation module 10 according to the present disclosure. Time reversal delays calculated by time reversal unit 8 and inspection parameters from inspection parameter storage unit 12 are input to a computer simulation software module 16. Computer simulation software within computer simulation software module 16 may be any suitable simulation software, such as a finite element analysis (FEA) calculator, or a commercially available simulation tool. The function of the computer simulation software is to use the time reversal delays to simulate beam propagation into the couplant medium (in an embodiment, water) and to compute the diffraction field of the acoustic wave front at a specific time, such as the time when the parallel wave front is incident on test surface 3. FIG. 4 shows an example of a diffraction field calculated by computer simulation software module 16.

Referring again to FIG. 1C, the computed diffraction field is input to a surface profile computation unit 20 which computes the surface profile using the wave front obtained from the diffraction field. The surface profile is obtained from the diffraction field at a time $t_0$ when the parallel wave front is incident on test surface 3, the time $t_0$ being given by the experimental data. In an embodiment, the coordinates of the part surface are determined by surface profile computation unit 20 using an image gradient technique commonly used in the computer vision field to detect edges and objects.

The computed diffraction field is also input to a coverage computation unit 22 which computes the coverage on test surface 3 using the diffraction field wave front amplitude at test surface 3, the coverage being defined as above threshold in those areas where the diffraction field amplitude at test surface 3 is above a user defined threshold value, and as sub-threshold in those areas where the diffraction field amplitude at test surface 3 is below the threshold value.

The time reversal delays, the inspection parameters and the surface profile are input to an aperture sensitivity computation unit 18, which computes the sensitivity of each receiver aperture to the reflected wave front emanating from corresponding sections of test surface 3. Aperture sensitivity computation unit 18 computes steering due to the time reversal delays and is thereby able to deduce the sections of test surface 3 from which echo signals are received at each receiver aperture. An amplitude compensation gain computation unit 24 uses the aperture sensitivity information to compute amplitude compensation gain to be applied to each receiver aperture.

Figure 2:
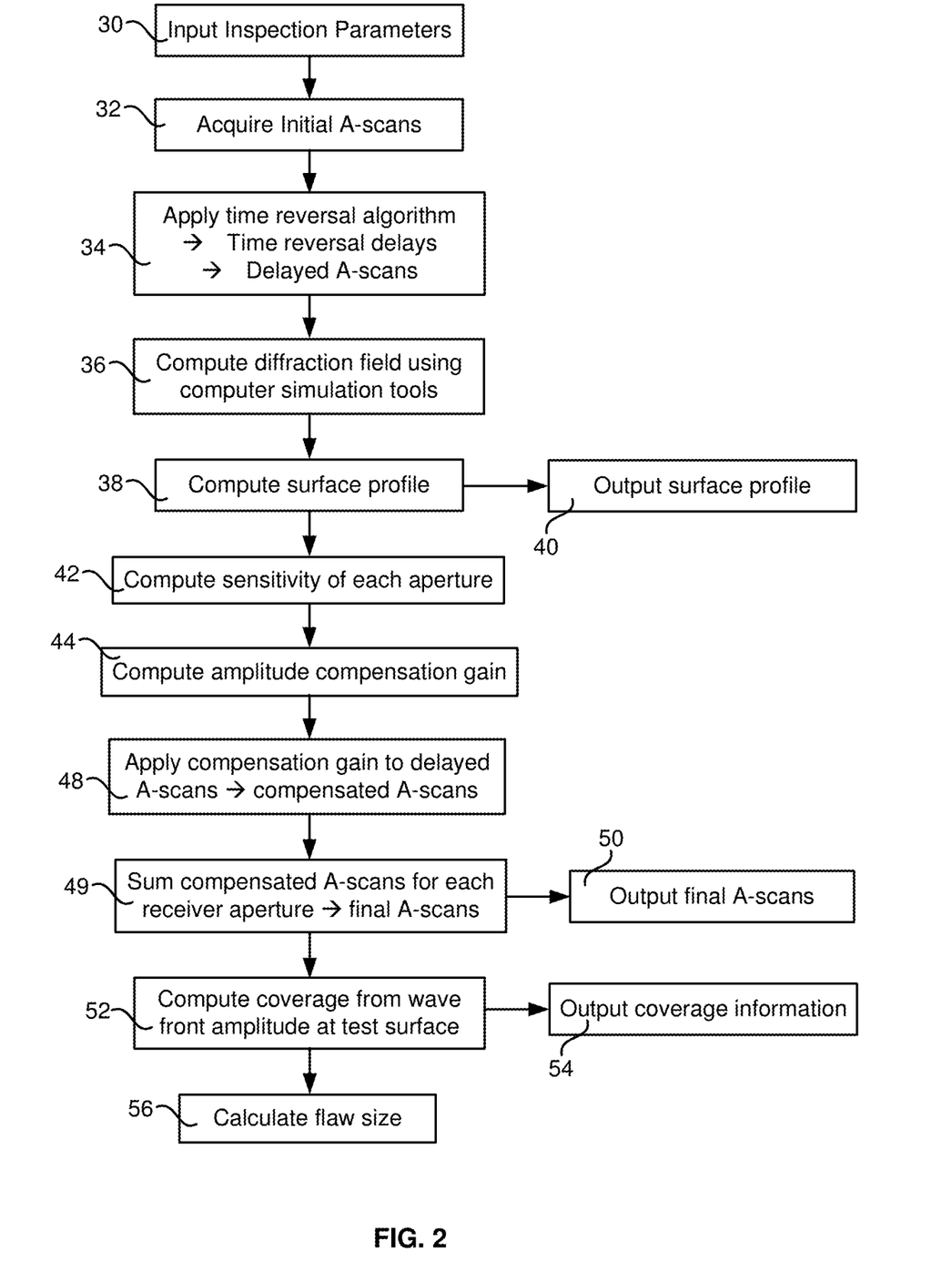
FIG. 2 is a schematic representation of an improved time reversal method according to the present disclosure.

FIG. 2 is a schematic representation of an improved time reversal method according to the present disclosure. In step 30, the inspection parameters are read from inspection parameter storage unit 12 and in step 32 the initial A-scans are acquired from probe 4 by acquisition unit 6. In step 34, the time reversal algorithm is applied, producing the time reversal delays which are applied to the initial A-scans to produce the delayed A-scans. In step 36, the diffraction field is computed using computer simulation software module 16, and in step 38 the surface profile is computed and output at step 40. In step 42, the sensitivity of each receiver aperture is computed, and in step 44 the amplitude compensation gain is computed. In step 48, the compensation gain is applied to the delayed A-scans producing compensated A-scans. In step 49 the compensated A-scans are summed for each receiver aperture producing final A-scans which are output at step 50. In step 52, the coverage is computed from the wave front amplitude at test surface 3, and the coverage information is output at step 54. In step 56 the size of a detected flaw is calculated using the final A-scans, the test surface profile and the inspection parameters.

Note that in a second embodiment of the method of FIG. 2, the step of summing A-scans may be performed before the step of applying compensation gain.

Figure 3A:
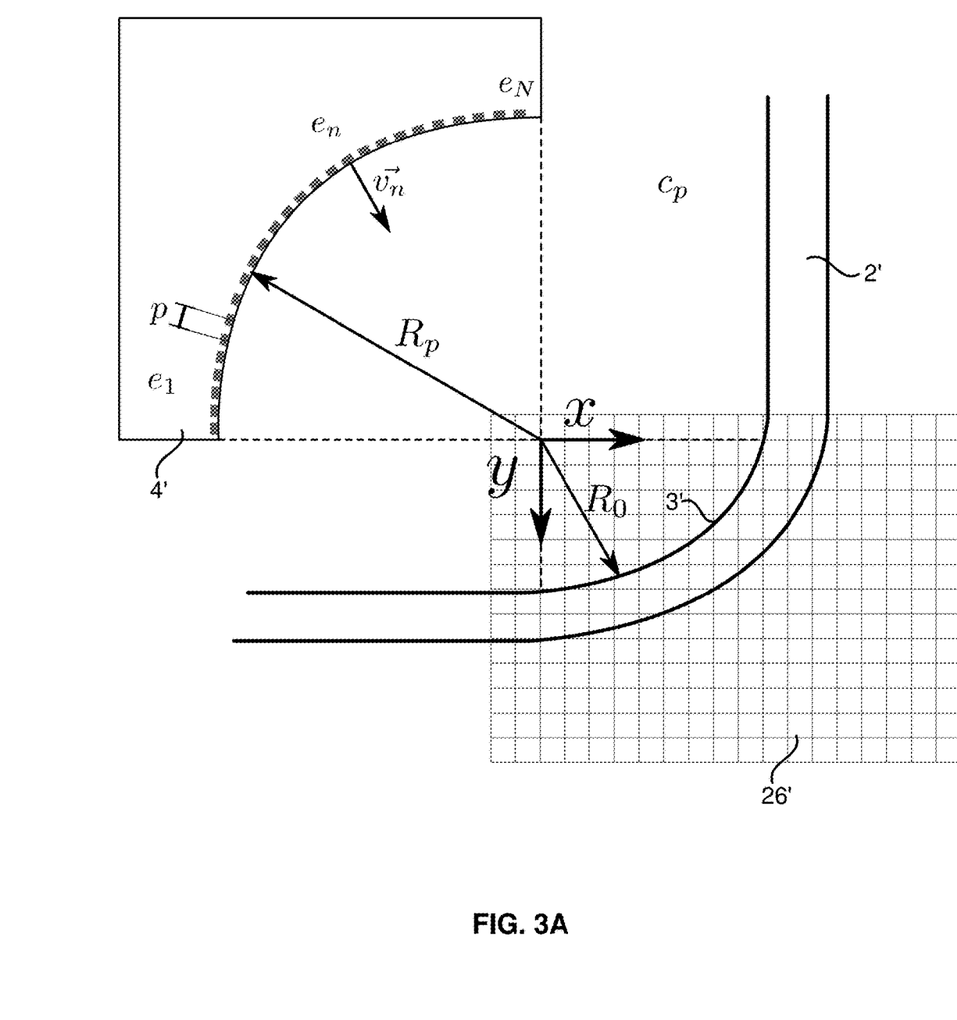
FIG. 3A is a schematic representation of inspection parameters for a curved probe array inspecting an inside corner of a test object.

FIG. 3A is a schematic representation of inspection parameters for a curved probe 4' inspecting an inside corner test surface 3' of a test object 2'. A computational mesh grid 26' is created for use in computations of the diffraction fields in the couplant and the test object. As illustrated in FIG. 3A, the following are the inspection parameters for this geometry:

N—Total number of probe elements
n—Probe element number, n=1, 2, . . . N
$e_n$—Position of element n
$\vec{v}_n$—Nominal propagation direction of element n
$c_p$—Sound velocity in couplant
$R_0$—Nominal test surface radius
$R_p$—Probe radius
p—Center-to-center distance between probe elements The inspection parameters also include user-selected transmitter and receiver apertures.

Figure 3B:
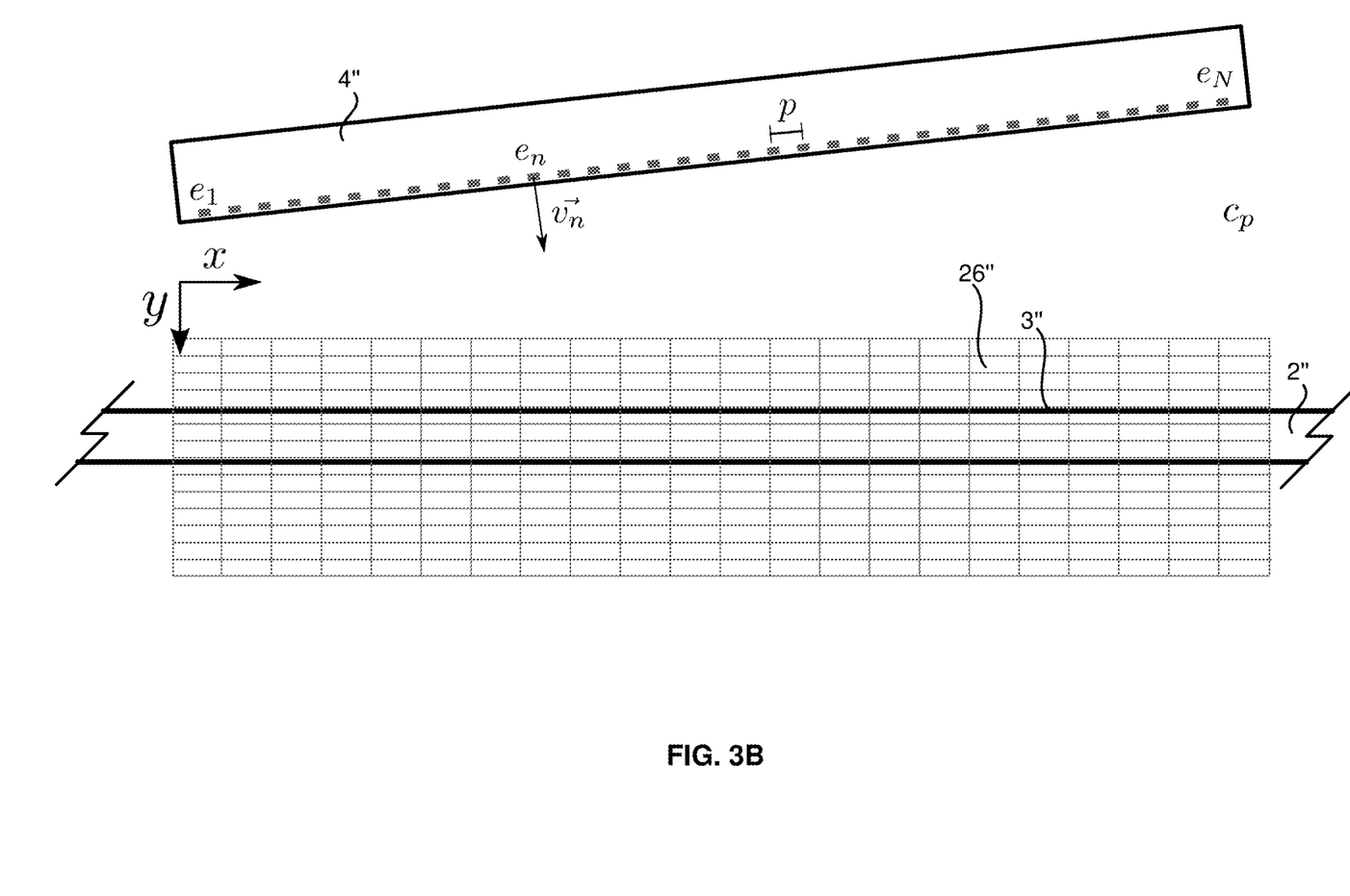
FIG. 3B is a schematic representation of inspection parameters for a planar probe array inspecting a planar test surface.

FIG. 3B is a schematic representation of inspection parameters for a planar probe 4" inspecting a planar test surface 3" of a test object 2". A computational mesh grid 26" is created for use in computations of the diffraction fields in the couplant and the test object. As illustrated in FIG. 3B, the following are the inspection parameters for this geometry:

N—Total number of probe elements
n—Probe element number, n=1, 2, . . . . . N
$e_n$—Position of element n
$\vec{v}_n$—Nominal propagation direction of element n
$c_p$—Sound velocity in couplant
p—Center-to-center distance between probe elements The inspection parameters also include user-selected transmitter and receiver apertures.

FIG. 4 is a plot of the diffraction field of a wave front at time $t_0$, where time $t_0$ is the time of incidence of the wave front on inside corner test surface 3'. The plot is a summation of each of the single aperture diffraction fields. The wave front has normal incidence to test surface 3', meaning that the wave front profile is parallel to the profile of test surface 3'. At time $t_0$ the wave front profile is also coincident with test surface 3'.

Figure 5:
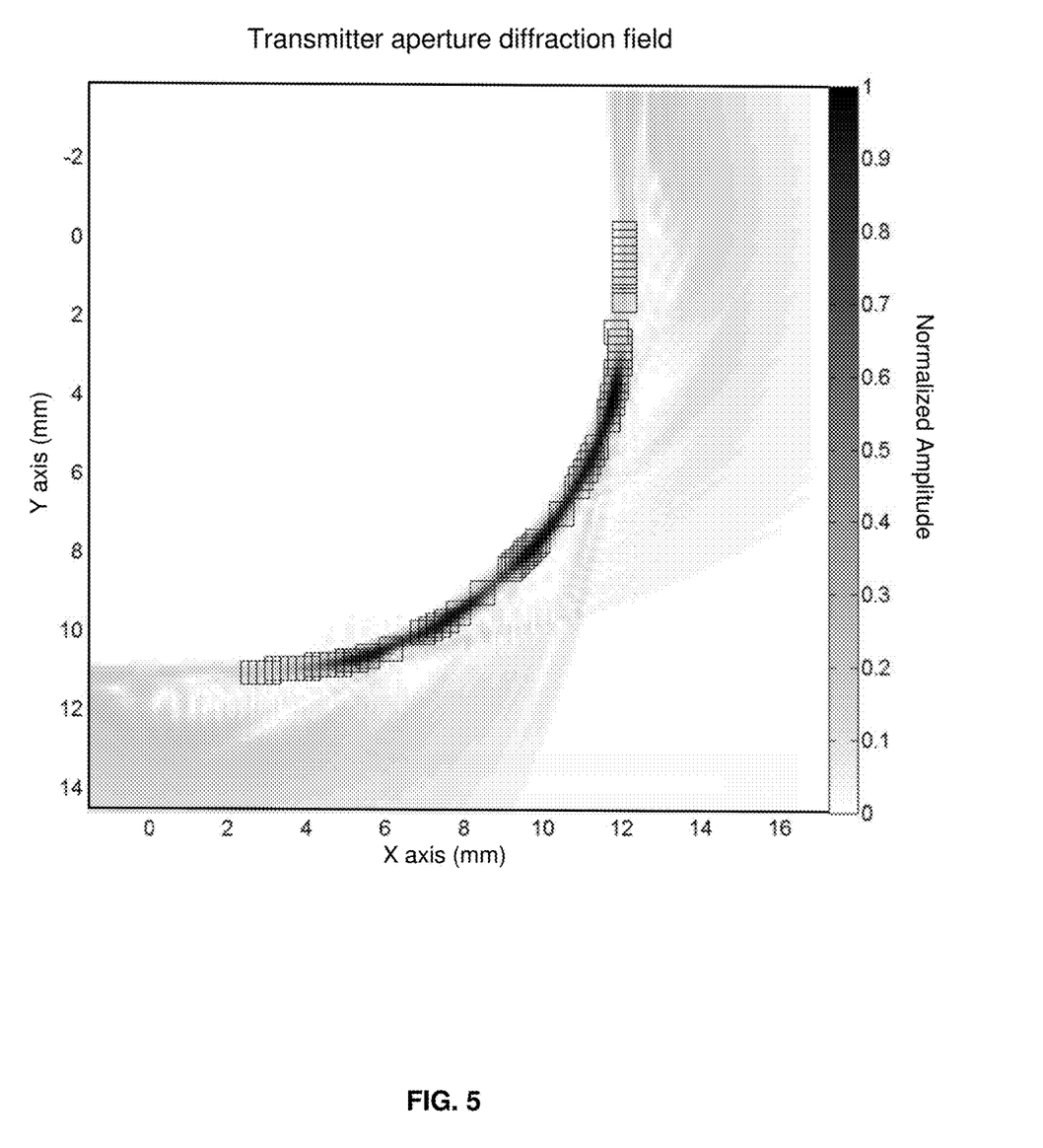
FIG. 5 is an illustration showing the test surface profile determined from the transmitter aperture diffraction field for the curved probe illustrated in FIG. 3A.

FIG. 5 illustrates how the profile of test surface 3' may be determined from the transmitter aperture diffraction field. In the embodiment of FIG. 5, the surface profile is detected using an image gradient algorithm, which detects the surface using the first derivatives of the diffraction field at time $t_0$. The square boxes represent areas used to determine an average gradient at each position. The center of each box is the point which is deemed to be on the test surface. Note that the image gradient algorithm is one method of determining the test surface profile, but other methods may also be used to determine the surface profile from the diffraction field, and all such methods are within the scope of the present disclosure.

Figure 6:
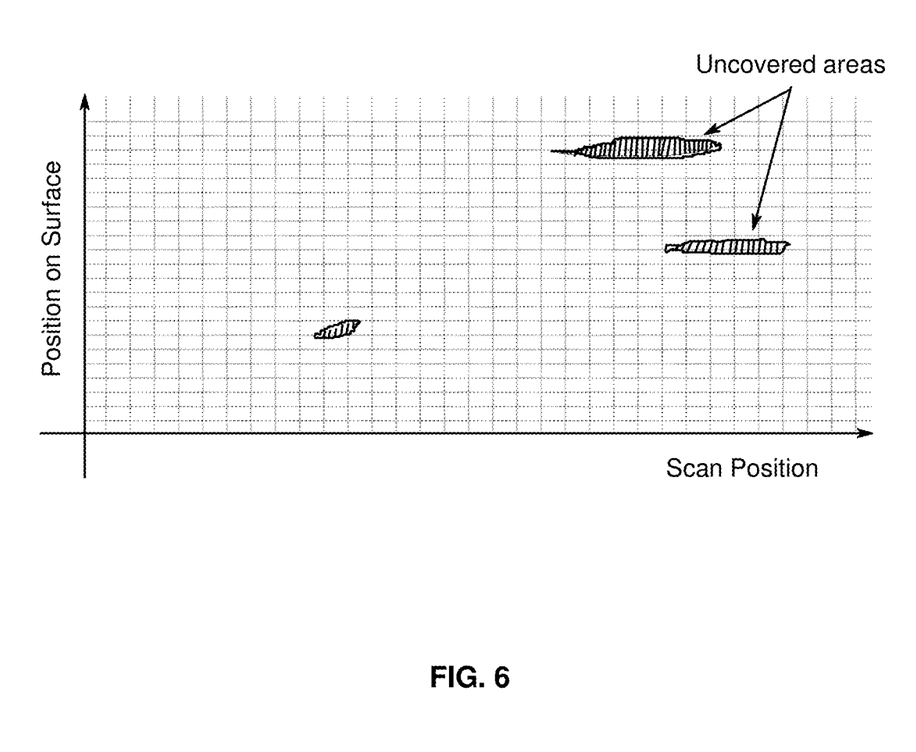
FIG. 6 is a schematic representation of coverage mapping on a test surface.

FIG. 6 is a schematic representation of coverage mapping on test surface 3, in which the shaded areas represent areas on test surface 3 where the coverage is below threshold. Areas with sub-threshold coverage are defined as those areas where the amplitude of the diffraction field at test surface 3 is below a user-defined threshold, the user-defined threshold being defined relative to the maximum diffraction field amplitude. Note that the coverage information obtained with the system of FIGS. 1A, 1B and 1C and the method of FIG. 2, is derived at a single scan position and therefore represents a single vertical data line in FIG. 6, in which certain surface positions have sub-threshold coverage. The map of FIG. 6 is a compilation of all such lines at all probe scan positions.

Those skilled in the art should appreciate that deducing time reversal delays may include the study of sound paths generated by other combinations of transmitting and receiving elements, and all such combinations are within the scope of the present disclosure.

Those skilled in the art should also appreciate that deducing time reversal delays may include other methods of correlating sound paths and times of flights which all are within the scope of the present disclosure.

Although the present invention has been described in relation to particular embodiments thereof, it can be appreciated that various designs can be conceived based on the teachings of the present disclosure, and all are within the scope of the present disclosure.

What is claimed is:

1. An ultrasound inspection system comprising:
  a phased array probe acoustically coupled to a test surface of a test object, the probe comprising probe elements, the probe elements comprising transmitting elements configured to transmit acoustic energy into the test surface and receiving elements configured to receive echo signals, the echo signals comprising surface echo signals from the test surface and flaw echo signals from flaws in the test object;
  an acquisition unit configured to receive the echo signals and to produce initial A-scans, wherein there is one initial A-scan for each one of the receiving elements;

a time reversal unit configured to compute time reversal delays from surface echo signal arrival times and to apply the time reversal delays to the corresponding transmitting elements, thereby forming a transmitted wave front parallel to the test surface, the echo signals from the transmitted wave front producing delayed A-scans, wherein there is one delayed A-scan for each one of the receiving elements;

an inspection parameter storage unit configured to store inspection parameters of the inspection system;

a computation module configured to compute a diffraction field of the transmitted wave front; and, a surface profile computation unit configured to compute a test surface profile based on the diffraction field at a time of incidence of the transmitted wave front at the test surface.

2. The inspection system of claim 1 wherein the transmitting elements are grouped into at least one transmitter aperture and the receiving elements are grouped into at least one receiver aperture.

3. The inspection system of claim 2 wherein the at least one transmitter aperture is one transmitter aperture comprising all the probe elements.

4. The inspection system of claim 2 wherein the computation module further comprises an aperture sensitivity computation unit configured to use the time reversal delays, the inspection parameters, the test surface profile and the diffraction field to compute test surface sections, wherein the echo signals from each of the test surface sections are received by a corresponding one of the at least one receiver aperture.

5. The inspection system of claim 2 wherein the computation module further comprises an amplitude compensation gain computation unit configured to compute an amplitude compensation gain for each of the at least one receiver aperture.

6. The inspection system of claim 5 further comprising an amplitude compensation unit configured to apply the amplitude compensation gain to each of the delayed A-scans, thereby producing compensated A-scans.

7. The inspection system of claim 6 further comprising an aperture summation unit configured to sum the compensated A-scans corresponding to each one of the at least one receiver aperture, thereby producing final A-scans, wherein there is one final A-scan corresponding to each one of the at least one receiver aperture.

8. The inspection system of claim 7 further comprising a coverage computation unit configured to compute a coverage value for a selected test surface section, wherein the coverage number is sub-threshold if the amplitude of the diffraction field at the test surface is less than a user defined threshold, and the coverage number is above threshold if the amplitude of the diffraction field at the test surface is greater than or equal to the user defined threshold.

9. The inspection system of claim 7 further comprising a flaw sizing unit configured to compute a flaw size from the flaw echo signals, the final A-scans, the test surface profile and the inspection parameters.

10. The inspection system of claim 1 further comprising a computer simulation software module configured to calculate the diffraction field from the inspection parameters and the time reversal delays.

11. The inspection system of claim 10 wherein the computer simulation software module is a finite element analysis software module.

12. A method of time reversal inspection with an ultrasound inspection system comprising a phased array probe acoustically coupled to a test surface of a test object, the probe comprising probe elements, the probe elements comprising transmitting elements configured to transmit acoustic energy into the test surface and receiving elements configured to receive echo signals, the echo signals comprising surface echo signals from the test surface and flaw echo signals from flaws in the test object, the method comprising the steps of:

obtaining inspection parameters defining the geometry of the inspection system;

acquiring initial A-scans, wherein the initial A-scans are plots of echo signal amplitudes against echo signal arrival times, and wherein there is one initial A-scan for each one of the receiving elements;

computing time reversal delays from surface echo signal arrival times, each of the surface echo signal arrival times corresponding to arrival of a surface echo signal at a corresponding receiving element from a corresponding transmitting element;

applying the time reversal delays to the corresponding transmitting elements, thereby forming a transmitted wave front parallel to the test surface, the echo signals from the transmitted wave front producing delayed A-scans, wherein there is one delayed A-scan for each one of the receiving elements;

computing a diffraction field of the transmitted wave front; and, computing a test surface profile, the test surface profile being computed from the diffraction field at a time of incidence of the transmitted wave front at the test surface.

13. The method of claim 12 wherein the transmitting elements are grouped into at least one transmitter aperture and the receiving elements are grouped into at least one receiver aperture.

14. The method of claim 13 wherein the at least one transmitter aperture is one transmitter aperture comprising all the probe elements.

15. The method of claim 13 further comprising the step of computing test surface sections using the time reversal delays, the inspection parameters, the test surface profile and the diffraction field, and wherein the echo signals from each of the test surface sections are received by a corresponding one of the at least one receiver aperture.

16. The method of claim 13 further comprising the step of computing an amplitude compensation gain for each of the at least one receiver aperture.

17. The method of claim 16 further comprising the step of applying the amplitude compensation gain to each of the delayed A-scans, thereby producing compensated A-scans.

18. The method of claim 17 further comprising the step of summing the compensated A-scans corresponding to each one of the at least one receiver aperture, thereby producing final A-scans, wherein there is one final A-scan corresponding to each one of the at least one receiver aperture.

19. The method of claim 18 further comprising the step of computing a coverage number for a selected test surface section, wherein the coverage number is sub-threshold if a diffraction field amplitude at the test surface is less than a user defined threshold, and the coverage number is above threshold if the diffraction field amplitude at the test surface is greater than or equal to the user defined threshold.

20. The method of claim 18 further comprising the step of computing a flaw size from the flaw echo signals, the final A-scans, the test surface profile and the inspection parameters.

21. The method of claim 12 further comprising the step of using a computer simulation software module to calculate the diffraction field from the inspection parameters and the time reversal delays.

22. The method of claim 21 wherein the computer simulation software module is a finite element analysis software module.

* * * * *